(12) United States Patent
Miettinen et al.

(10) Patent No.: US 10,702,708 B2
(45) Date of Patent: Jul. 7, 2020

(54) ACCOUNTING FOR IMAGING-BASED RADIATION DOSES

(71) Applicants: Varian Medical Systems, Inc., Palo Alto, CA (US); Varian Medical Systems International AG, Cham (CH)

(72) Inventors: Mika Miettinen, San Fransicso, CA (US); Stefan J. Thieme-Marti, Windisch (CH); Jeff Everett, Oakland, CA (US); Andres Graf, Oberwil (CH); Joakim Pyyry, Helsinki (FI); Juha Kauppinen, Espoo (FI)

(73) Assignees: Varian Medical Systems, Inc., Palo Alto, CA (US); Varian Medical Systems International AG, Steinhausen (CH)

( * ) Notice: Subject to any disclaimer, the term of this patent is extended or adjusted under 35 U.S.C. 154(b) by 701 days.

(21) Appl. No.: 14/865,821

(22) Filed: Sep. 25, 2015

(65) Prior Publication Data
US 2017/0087385 A1    Mar. 30, 2017

(51) Int. Cl.
*A61N 5/10* (2006.01)

(52) U.S. Cl.
CPC .............. *A61N 5/1037* (2013.01); *A61N 5/10* (2013.01); *A61N 5/103* (2013.01); *A61N 5/1031* (2013.01);
(Continued)

(58) Field of Classification Search
CPC ........ A61N 5/10; A61N 5/103; A61N 5/1031; A61N 5/1039; A61N 5/1048; A61N 5/1049; A61N 5/1061; A61N 5/1062; A61N 5/1071; A61N 2005/1072; A61N 2005/1061; A61N 2005/1062;
(Continued)

(56) References Cited

U.S. PATENT DOCUMENTS

| | | | | |
|---|---|---|---|---|
| 5,661,773 A | * | 8/1997 | Swerdloff | A61N 5/1042 378/65 |
| 5,754,622 A | * | 5/1998 | Hughes | G21K 1/04 378/108 |

(Continued)

OTHER PUBLICATIONS

4D Integrated Treatment Console Reference Guide (P/N 100015118-02); Varian Medical Systems, Inc.; Apr. 2004; 7 pages.
(Continued)

*Primary Examiner* — Allen C. Ho
(74) *Attorney, Agent, or Firm* — Fitch, Even, Tabin & Flannery LLP

(57) ABSTRACT

A radiation-treatment plan to treat a treatment target in a given patient takes into account imaging-based dosing of that patient by, for example, automatically accounting for radiation dosing of the given patient that results from imaging to determine at least one physical position of the given patient when forming the radiation-treatment plan. These teachings are particularly beneficial when applied in application settings where the aforementioned imaging comprises obtaining images using megavoltage-sourced radiation. By one approach these teachings provide for automatically accounting for radiation dosing of the given patient that results from imaging by, at least in part, automatically adjusting therapeutic dosing of the given patient as a function of the radiation dosing of the given patient that results from such imaging.

14 Claims, 2 Drawing Sheets

(52) U.S. Cl.
CPC ......... *A61N 5/1039* (2013.01); *A61N 5/1048* (2013.01); *A61N 5/1049* (2013.01); *A61N 5/1065* (2013.01); *A61N 5/1071* (2013.01); *A61N 5/1067* (2013.01); *A61N 2005/1054* (2013.01); *A61N 2005/1061* (2013.01); *A61N 2005/1062* (2013.01); *A61N 2005/1072* (2013.01)

(58) Field of Classification Search
CPC .......... A61N 5/1037; A61N 2005/1054; A61N 5/1064; A61N 5/1065; A61N 5/1067
USPC .......................................................... 378/65
See application file for complete search history.

(56) References Cited

U.S. PATENT DOCUMENTS

| | | | | |
|---|---|---|---|---|
| 5,870,697 | A * | 2/1999 | Chandler | A61N 5/1031 378/62 |
| 5,901,199 | A * | 5/1999 | Murphy | A61B 6/08 378/65 |
| 6,083,167 | A * | 7/2000 | Fox | A61N 5/1002 600/439 |
| 6,104,778 | A * | 8/2000 | Murad | A61B 6/08 378/206 |
| 6,118,848 | A * | 9/2000 | Reiffel | A61N 5/1049 378/162 |
| 6,148,272 | A * | 11/2000 | Bergstrom | A61N 5/1031 250/363.04 |
| 6,219,403 | B1 * | 4/2001 | Nishihara | A61N 5/1048 378/205 |
| 6,301,329 | B1 * | 10/2001 | Surridge | A61N 5/103 378/65 |
| 6,307,914 | B1 * | 10/2001 | Kunieda | A61B 6/12 378/65 |
| 6,516,046 | B1 * | 2/2003 | Fröhlich | A61B 6/04 378/205 |
| 6,865,253 | B2 * | 3/2005 | Blumhofer | A61B 6/547 378/205 |
| 6,990,175 | B2 * | 1/2006 | Nakashima | A61B 6/032 378/101 |
| 7,186,991 | B2 * | 3/2007 | Kato | A61N 5/103 250/492.1 |
| 7,204,640 | B2 * | 4/2007 | Fu | A61N 5/1049 378/205 |
| 7,221,733 | B1 * | 5/2007 | Takai | A61N 5/1042 378/65 |
| 7,266,176 | B2 * | 9/2007 | Allison | A61N 5/1031 378/205 |
| 7,289,599 | B2 * | 10/2007 | Seppi | A61N 5/103 378/65 |
| 7,343,189 | B2 * | 3/2008 | Kagermeier | A61B 6/08 378/20 |
| 7,369,645 | B2 * | 5/2008 | Lane | A61N 5/1031 378/65 |
| 7,412,029 | B2 * | 8/2008 | Myles | A61N 5/1049 378/65 |
| 7,432,510 | B2 * | 10/2008 | Yeo | A61N 5/1048 250/374 |
| 7,453,984 | B2 * | 11/2008 | Chen | A61N 5/1049 378/65 |
| 7,469,035 | B2 * | 12/2008 | Keall | A61N 5/1042 378/205 |
| 7,477,722 | B2 * | 1/2009 | Carrano | A61B 6/022 378/41 |
| 7,496,173 | B2 * | 2/2009 | Goldman | A61N 5/1031 378/65 |
| 7,507,975 | B2 * | 3/2009 | Mohr | A61N 5/1042 250/492.1 |
| 7,574,251 | B2 * | 8/2009 | Lu | A61N 5/103 600/411 |
| 7,609,810 | B2 * | 10/2009 | Yi | A61N 5/1049 378/65 |
| 7,620,147 | B2 * | 11/2009 | Gertner | A61N 5/10 378/145 |
| 7,639,853 | B2 * | 12/2009 | Olivera | A61N 5/103 382/128 |
| 7,639,854 | B2 * | 12/2009 | Schnarr | A61N 5/103 382/128 |
| 7,643,661 | B2 * | 1/2010 | Ruchala | A61N 5/103 382/128 |
| 7,693,257 | B2 * | 4/2010 | Allison | A61N 5/103 378/108 |
| 7,773,788 | B2 * | 8/2010 | Lu | A61N 5/103 382/128 |
| 7,986,768 | B2 * | 7/2011 | Nord | A61N 5/103 378/65 |
| 8,009,803 | B2 * | 8/2011 | Nord | A61N 5/103 378/65 |
| 8,073,102 | B2 * | 12/2011 | Fallone | A61N 5/103 378/65 |
| 8,073,103 | B2 * | 12/2011 | Otto | A61B 6/5241 378/65 |
| 8,121,252 | B2 * | 2/2012 | Nord | A61N 5/103 378/65 |
| 8,130,907 | B2 * | 3/2012 | Maurer, Jr. | A61B 6/12 378/65 |
| 8,222,616 | B2 * | 7/2012 | Lu | A61N 5/103 250/390.03 |
| 8,232,535 | B2 * | 7/2012 | Olivera | A61N 5/1042 250/491.1 |
| 8,238,520 | B2 * | 8/2012 | Nord | A61N 5/103 378/65 |
| 8,280,002 | B2 * | 10/2012 | Bani-Hashemi | A61N 5/1064 378/65 |
| 8,284,897 | B2 * | 10/2012 | Nord | A61N 5/1037 378/65 |
| 8,295,435 | B2 * | 10/2012 | Wang | A61N 5/10 378/65 |
| 8,295,436 | B2 * | 10/2012 | Nord | A61N 5/1036 378/65 |
| 8,325,878 | B2 * | 12/2012 | McNutt | A61N 5/1031 378/65 |
| 8,331,532 | B2 * | 12/2012 | Nord | A61N 5/1037 378/65 |
| 8,406,844 | B2 * | 3/2013 | Ruchala | A61N 5/103 378/65 |
| 8,416,917 | B2 * | 4/2013 | Maltz | A61N 5/10 378/65 |
| 8,416,918 | B2 * | 4/2013 | Nord | A61N 5/1031 378/65 |
| 8,467,497 | B2 * | 6/2013 | Lu | A61N 5/1049 378/65 |
| 8,483,358 | B2 * | 7/2013 | Allison | A61B 6/00 378/65 |
| 8,509,383 | B2 * | 8/2013 | Lu | A61N 5/1049 378/65 |
| 8,559,596 | B2 * | 10/2013 | Thomson | G06T 7/0014 378/20 |
| 8,565,377 | B2 * | 10/2013 | Robar | A61N 5/1049 378/62 |
| 8,613,694 | B2 * | 12/2013 | Walsh | A61N 5/103 378/65 |
| 8,619,945 | B2 * | 12/2013 | Stahl | A61N 5/1037 378/64 |
| 8,693,630 | B2 * | 4/2014 | Nord | A61N 5/1031 378/65 |
| 8,699,664 | B2 * | 4/2014 | Otto | A61N 5/1067 378/65 |
| 8,712,012 | B2 * | 4/2014 | O'Connor | A61B 6/03 378/208 |
| 8,751,200 | B2 * | 6/2014 | Takai | G06Q 50/22 378/65 |
| 8,755,489 | B2 * | 6/2014 | Lavi | A61N 5/103 378/207 |
| 8,767,917 | B2 * | 7/2014 | Ruchala | A61N 5/103 378/65 |
| 8,772,742 | B2 * | 7/2014 | Rietzel | A61N 5/103 250/492.3 |

(56) References Cited

U.S. PATENT DOCUMENTS

| | | | |
|---|---|---|---|
| 8,791,418 B2* | 7/2014 | Visconti | G01T 1/00 |
| | | | 250/370.01 |
| 8,824,630 B2* | 9/2014 | Maurer, Jr. | G06F 19/3481 |
| | | | 378/20 |
| 8,831,706 B2* | 9/2014 | Fu | A61B 6/032 |
| | | | 378/65 |
| 8,837,674 B2* | 9/2014 | Ruan | A61N 5/1049 |
| | | | 378/65 |
| 8,861,672 B2* | 10/2014 | Maltz | A61B 6/032 |
| | | | 378/4 |
| 8,874,187 B2* | 10/2014 | Thomson | A61B 6/037 |
| | | | 378/62 |
| 8,971,489 B2* | 3/2015 | Ruan | A61N 5/1031 |
| | | | 378/151 |
| 8,983,031 B2* | 3/2015 | Rau | A61N 5/1037 |
| | | | 378/65 |
| 8,989,350 B2* | 3/2015 | Shibuya | A61N 5/1065 |
| | | | 378/205 |
| 9,014,454 B2* | 4/2015 | Zankowski | G06T 7/33 |
| | | | 382/132 |
| 9,155,907 B2* | 10/2015 | Kauppinen | A61N 5/103 |
| 9,387,345 B2* | 7/2016 | Nord | A61N 5/1031 |
| 9,616,251 B2* | 4/2017 | Filiberti | A61N 5/1075 |
| 9,750,955 B2* | 9/2017 | McNutt | A61N 5/1031 |
| 9,764,162 B1* | 9/2017 | Willcut | G06F 19/30 |
| 9,782,607 B2* | 10/2017 | Wiersma | A61N 5/1039 |
| 9,827,445 B2* | 11/2017 | Cordero Marcos | A61N 5/1031 |
| 10,475,537 B2* | 11/2019 | Purdie | G06F 19/3481 |

OTHER PUBLICATIONS

Grelewicz, Zachary et al.; "Combined MV + kV Inverse Treatment Planning for Optimal kV Dose Incorporation in IGRT," Physics in Medicine and Biology 59 (2014) pp. 1607-1621; IOP Publishing, Institute of Physics and Engineering in Medicine.

* cited by examiner

ACCOUNTING FOR IMAGING-BASED RADIATION DOSES

TECHNICAL FIELD

These teachings relate generally to the use of radiation as a therapeutic treatment and more specifically to the formation and use of corresponding radiation-treatment plans.

BACKGROUND

The use of radiation to treat medical conditions comprises a known area of prior art endeavor. For example, radiation therapy comprises an important component of many treatment plans for reducing or eliminating unwanted tumors. Unfortunately, applied radiation does not inherently discriminate between unwanted areas and adjacent healthy tissues, organs, or the like that are desired or even critical to continued survival of the patient. As a result, radiation is ordinarily applied in a carefully administered manner to at least attempt to restrict the radiation to a given target volume.

Treatment plans typically serve to specify any number of operating parameters as pertain to the administration of such treatment with respect to a given patient. Such treatment plans are often optimized prior to use. (As used herein, "optimization" will be understood to refer to improving upon a candidate treatment plan without necessarily ensuring that the optimized result is, in fact, the singular best solution.) Many optimization approaches use an automated incremental methodology where various optimization results are calculated and tested in turn using a variety of automatically-modified (i.e., "incremented") treatment plan optimization parameters.

Generally speaking, a well-conceived radiation-treatment plan serves to help ensure that the treatment target receives a prescribed dose of radiation while avoiding, to as large an extent as might be possible, undue dosing of surrounding or intervening tissues and organs. Unfortunately, the therapeutic radiation being used to so treat the patient is often not the only source of radiation dosing in a modern treatment facility.

For example, as part of ensuring that the therapeutic radiation beam is properly administered it can be very important to be certain of the patient's position and orientation. Even the most carefully conceived radiation-treatment plan can be rendered less effective if the patient's treatment volume moves or otherwise changes in unanticipated ways. Accordingly, images of the patient that are formed using megavoltage energies are becoming more common as such images provide helpful information regarding such positioning.

That image-forming energy, however, is radiation that may be over and above whatever carefully determined dosing is anticipated by the radiation-treatment plan. In some cases the administering technicians or other medical services providers attempt to manually account for such incidental radiation when managing the formation of their radiation-treatment plans. In other cases the issue simply goes unaddressed.

BRIEF DESCRIPTION OF THE DRAWINGS

The above needs are at least partially met through provision of the accounting for imaging-based radiation doses described in the following detailed description, particularly when studied in conjunction with the drawings, wherein.

Figure 1:
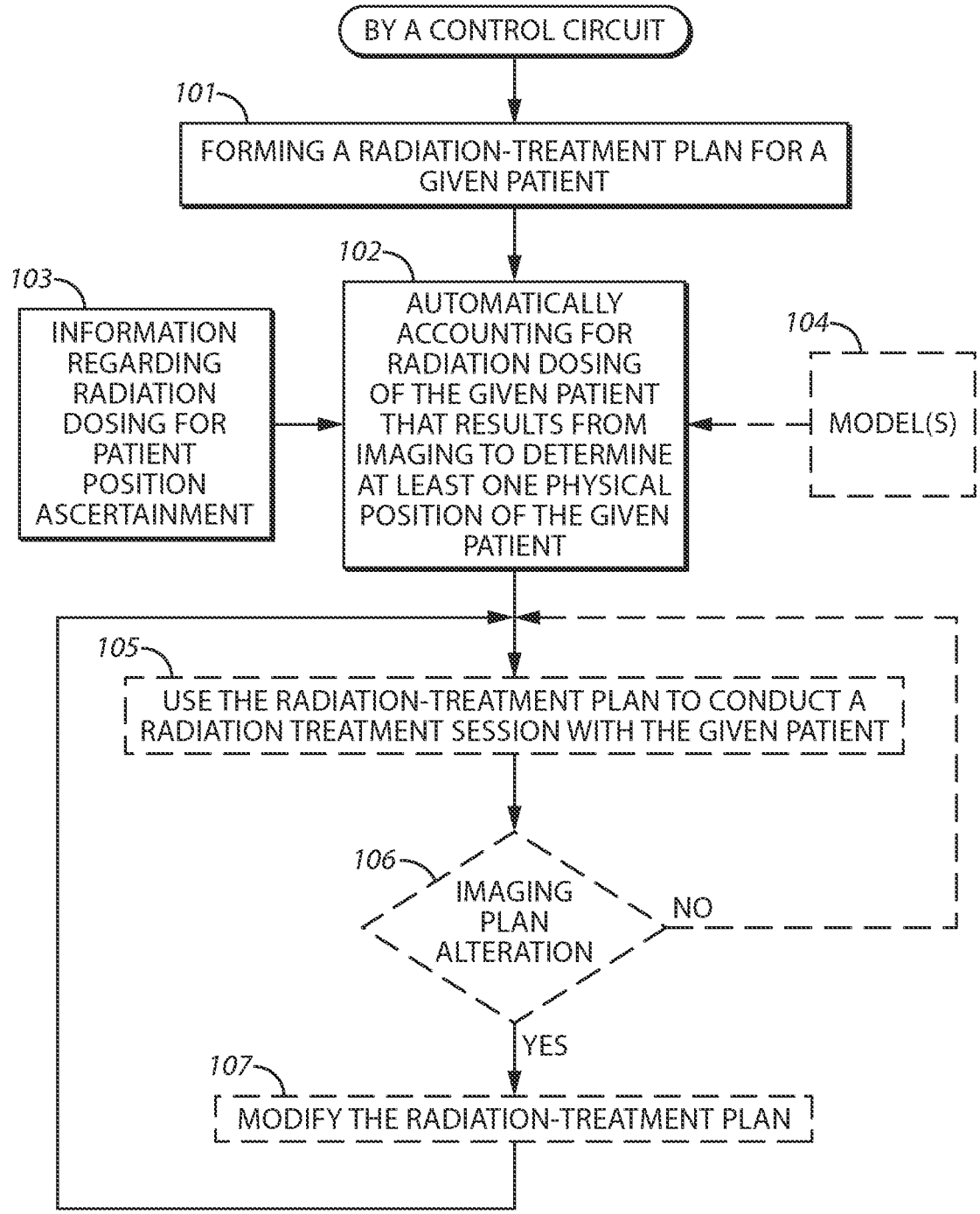
FIG. 1 comprises a flow diagram as configured in accordance with various embodiments of these teachings.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present teachings. Also, common but well-understood elements that are useful or necessary in a commercially feasible embodiment are often not depicted in order to facilitate a less obstructed view of these various embodiments of the present teachings. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, these various embodiments serve to facilitate using a radiation-treatment plan to treat a treatment target in a given patient that takes into account imaging-based dosing of that patient. More particularly, these embodiments provide for automatically accounting for radiation dosing of the given patient that results from imaging to determine at least one physical position of the given patient when forming the radiation-treatment plan. These teachings are particularly beneficial when applied in application settings where the aforementioned imaging comprises obtaining images using megavoltage-sourced radiation. By one approach these teachings provide for automatically accounting for radiation dosing of the given patient that results from imaging by, at least in part, automatically adjusting therapeutic dosing of the given patient as a function of the radiation dosing of the given patient that results from such imaging.

By one approach these teachings provide for using at least one imaging dose model to determine a corresponding radiation dose that can be attributed to the imaging.

These teachings are highly flexible in practice and will accommodate a variety of modifications as desired. For example, by one approach, these teachings will accommodate accounting for multiple instances of imaging that each have a corresponding radiation dosing of the given patient. If desired, these multiple instances can include prospective and/or completed instances of such imaging.

Such a radiation-treatment plan can then be used to conduct a radiation treatment session with the given patient. If desired, these teachings will further accommodate detecting an alteration to an imaging plan as corresponds to that radiation treatment session. Upon detecting such an alteration (which might comprise, for example, adding an additional imaging episode for that radiation treatment session and/or skipping one or more imaging episodes for that radiation concession) the radiation-treatment plan can be automatically modified to reflect the reduced or additional imaging-based dosing and then continue for the remainder of the radiation treatment session.

So configured, imaging-based dosing can be accounted for when creating and/or assessing a given radiation treatment plan and can further be monitored during a current course of treatment to facilitate further corresponding modifications to the radiation treatment plan. Employing these teachings can free medical service providers and technicians from an often laborious attempt to at least partially reflect such imaging-based dosing activities when forming and/or administering a radiation treatment plan while simultaneously typically assuring better accuracy and hence a better result for the patient.

Figure 2:
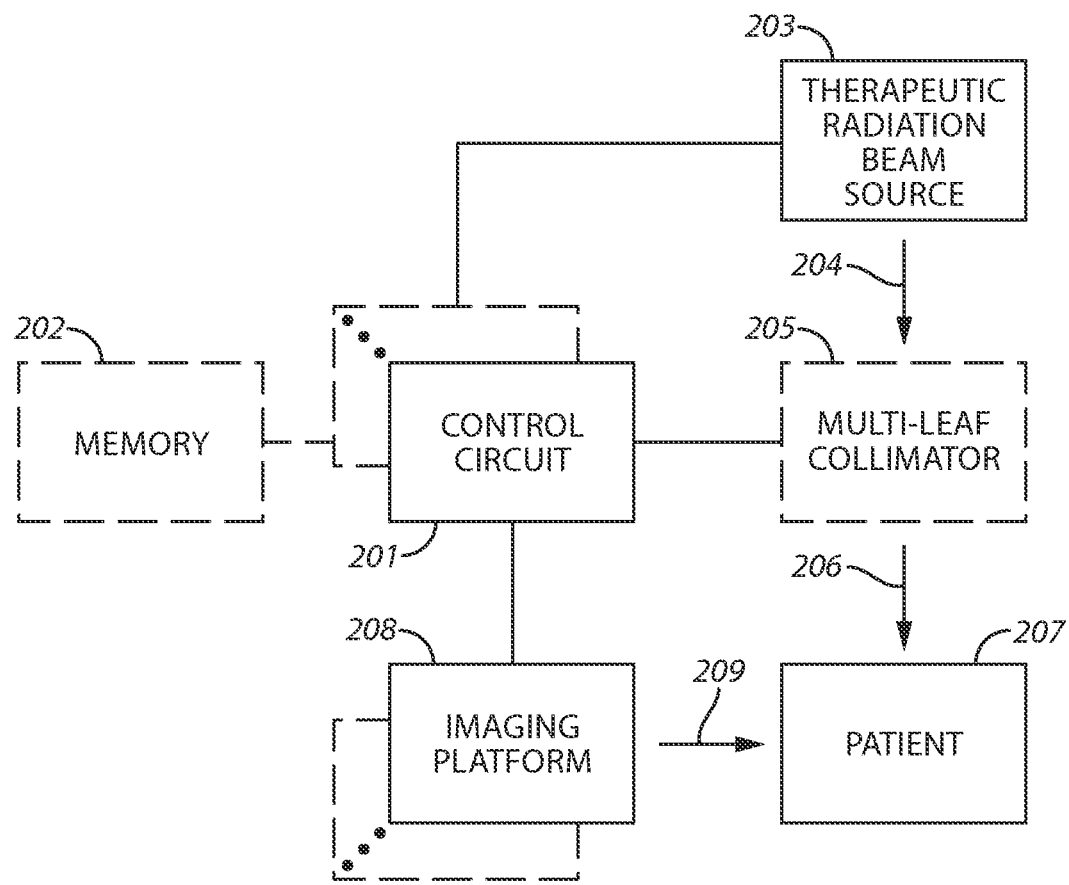
FIG. 2 comprises a block diagram as configured in accordance with various embodiments of these teachings.

These and other benefits may become clearer upon making a thorough review and study of the following detailed description. Referring now to the drawings, and in particular to FIG. 1, an illustrative process 100 that is compatible with many of these teachings will now be presented. For the sake of an illustrative example it will be presumed in this description that a control circuit (or plurality of control circuits) carries out the actions, steps, and functions described in this process 100. FIG. 2 provides an illustrative example in these regards.

As shown in FIG. 2, a radiation therapy treatment platform 200 can include or otherwise operably couple to a control circuit 201. Being a "circuit," the control circuit 201 therefore comprises structure that includes at least one (and typically many) electrically-conductive paths (such as paths comprised of a conductive metal such as copper or silver) that convey electricity in an ordered manner, which path(s) will also typically include corresponding electrical components (both passive (such as resistors and capacitors) and active (such as any of a variety of semiconductor-based devices) as appropriate) to permit the circuit to effect the control aspect of these teachings.

Such a control circuit 201 can comprise a fixed-purpose hard-wired hardware platform (including but not limited to an application-specific integrated circuit (ASIC) (which is an integrated circuit that is customized by design for a particular use, rather than intended for general-purpose use), a field-programmable gate array (FPGA), and the like) or can comprise a partially or wholly-programmable hardware platform (including but not limited to microcontrollers, microprocessors, and the like). These architectural options for such structures are well known and understood in the art and require no further description here. This control circuit 201 is configured (for example, by using corresponding programming as will be well understood by those skilled in the art) to carry out one or more of the steps, actions, and/or functions described herein. It will also be understood that a "control circuit" can comprise multiple such components or platforms as well as suggested by the phantom control circuit box in FIG. 2.

By one optional approach the control circuit 201 operably couples to a memory 202. This memory 202 may be integral to the control circuit 201 or can be physically discrete (in whole or in part) from the control circuit 201 as desired. This memory 202 can also be local with respect to the control circuit 201 (where, for example, both share a common circuit board, chassis, power supply, and/or housing) or can be partially or wholly remote with respect to the control circuit 201 (where, for example, the memory 202 is physically located in another facility, metropolitan area, or even country as compared to the control circuit 201).

In addition to radiation treatment plans this memory 202 can serve, for example, to non-transitorily store the computer instructions that, when executed by the control circuit 201, cause the control circuit 201 to behave as described herein. (As used herein, this reference to "non-transitorily" will be understood to refer to a non-ephemeral state for the stored contents (and hence excludes when the stored contents merely constitute signals or waves) rather than volatility of the storage media itself and hence includes both non-volatile memory (such as read-only memory (ROM) as well as volatile memory (such as an erasable programmable read-only memory (EPROM).)

The radiation therapy treatment platform 200 also includes a therapeutic radiation beam source 203 that operably couples and responds to the control circuit 201. So configured, a corresponding radiation beam 204 as emitted by the therapeutic radiation beam source 203 can be selectively switched on and off by the control circuit 201. These teachings will also accommodate having the control circuit 201 control the relative strength of the radiation beam 204. Radiation sources are well understood in the art and require no further description here.

In this example the radiation beam 204 is directed towards a multi-leaf collimation system 205 that also operably couples to the control circuit 201. Multi-leaf collimators are comprised of a plurality of individual parts (known as "leaves") that are formed of a high atomic numbered material (such as tungsten) that can move independently in and out of the path of the radiation-therapy beam in order to selectively block (and hence shape) the beam. Typically the leaves of a multi-leaf collimator are organized in pairs that are aligned collinearly with respect to one another and that can selectively move towards and away from one another via controlled motors.

By passing a radiation beam 204 through the aperture(s) of a multi-leaf collimator the radiation beam 204 can be modulated to provide a modulated radiation beam 206 that better matches the dosing requirements of the treatment session. These dosing requirements typically include (or at least presume) prescribing which body tissues to irradiate and which body tissues to avoid irradiating. to thereby permit the control circuit 201 to control movement of the leaves of the multi-leaf collimation system 205 and hence the formation and distribution of one or more radiation-modulating apertures. The resultant modulated radiation beam 206 then reaches a treatment target in a corresponding patient 207.

In this illustrative example the radiation therapy treatment platform 200 also includes at least one imaging platform 208. For the sake of this example the imaging platform 208 is presumed to utilize megavoltage-range radiation (such as but not limited to x-rays) 209 to form one or more corresponding images that include, at least in part, the patient 207. These teachings will accommodate a number of variations in these regards. By one approach, for example, only a single such image for a given radiation treatment session may be acquired. By another approach, a plurality of such images may be acquired during a single radiation treatment session (or immediately prior thereto) where some or all of the images are acquired using different imaging-beam locations vis-à-vis the patient 207. It will also be understood that some of these images may be captured using one level of energy while other images are acquired using a different level of energy. It is also contemplated that a plurality of such images may be acquired using two or more imaging platforms 208 that differ from one another with respect to their location, energy level, and/or image-capture modalities.

With continuing reference to both FIGS. 1 and 2, this process 100 begins, at block 101, with forming a radiation-treatment plan for a given patient 207. As noted above, various general approaches to forming a radiation-treatment plan involving automated optimization with respect to one or more treatment parameters as pertain to the treatment platform itself are well known in the art. For the sake of clarity and simplicity elaboration in those regards is not provided here.

At block 102 this process 100 provides for automatically accounting for radiation dosing of the given patient 207 that results from imaging to determine at least one physical position of the given patient 207. More specifically, this activity can comprise, at least in part, optimizing the radiation-treatment plan while also accounting for the radiation dosing of the given patient that results from such imaging. For example, the imaging dose distribution can be incorporated into and thereby taken into account as part of the base dose distribution. So configured, the final, total planned dose distribution resulting from both imaging fields and treatment fields will more likely meet the clinician's dose objectives for the target volume and untargeted patient volumes.

This process 100 will accommodate various specific approaches as regards the relevant "physical position" of the patient 207. By one approach, for example, the image may convey information regarding a specific physical position of the patient 207 upon a corresponding couch in the treatment area. By another approach, and as another example, the image may provide information regarding a relative position of a treatment target within the patient 207 vis-à-vis, for example, other anatomical structures or markers.

The process 100 provides in this example for drawing upon information 103 regarding radiation dosing to which the patient 207 was exposed when one or more of the imaging platforms 208 utilized radiation to ascertain the aforementioned patient position. By one approach this information is previously acquired and available in the aforementioned memory 202. By another approach, some or all of this information is pulled at a time of need from an original source of the information (such as the imaging platform 208 itself) or from an intervening repository of such information as desired.

By one approach, the information regarding such radiation dosing of the given patient during imaging activity is expressed in, or converted into, Monitor Units (MU's). Monitor Units are often employed in the art during radiation treatment plan optimization either directly or indirectly and hence constitute a convenient metric for these purposes.

By one approach, this information 103 can represent only a single or multiple instances of such imaging. In the case of multiple instances of imaging, these teachings will accommodate accounting for the radiation dosing of the given patient 207 corresponding to each such imaging instance. When accounting for multiple instances of imaging, if desired, this information 103 can include information regarding actual imaging-beam locations (for example, the location of the imaging-beam source with respect to the patient and/or a location of the imaging beam where exposure to the patient 207 occurs). When accounting for actual imaging-beam locations, if desired these teachings will further support the information 103 including actual imaging-beam locations on a patient setup-by-setup basis (to account for variations in these regards that can occur from one treatment facility to another or from one treatment session to another in the same facility).

When accounting for multiple instances of imaging, if desired, this information 103 can also include information regarding prospective and/or completed instances of the imaging. Completed imaging instances can include imaging that occurred just prior to the immediate radiation treatment session (for example, that same day or within the one or two hours that precede the treatment session) and/or imaging that occurred during or otherwise associated with prior completed radiation treatment sessions for this patient 207 (for example, that occurred on a previous day). Prospective imaging instances, in turn, can include imaging that is scheduled or otherwise likely or anticipated to occur during the radiation treatment session that corresponds to the present radiation-treatment plan and/or imaging that is scheduled or otherwise likely or anticipated to occur in conjunction with future radiation treatment sessions.

As noted above, the information 103 regarding radiation dosing for patient position ascertainment can include, at least in part, information regarding actual imaging-beam locations (and other relevant information such as energy levels for the imaging beams). In such a case, automatically accounting for such radiation dosing can comprise using that actual imaging-beam location information to estimate corresponding radiation dosages experienced by the patient 207. By one approach, the process 100 has access to one or more models 104 such as one or more relevant radiobiological models. In such a case the process 100 will accommodate using a relevant imaging dose model to determine a radiation dose that is due to a particular imaging event. A radiobiological model can be particularly useful to estimate a cumulative effective radiation dose in particular tumors, tissues, organs, and other anatomical features. For example, a radiobiological model can serve to estimate a cumulative effective radiation dose based upon a plurality of imaging episodes that use at least partially-different actual imaging-beam locations where, for example, the effective radiation dose experienced by a particular patient volume can vary for a variety of reasons from one imaging-beam location to another.

By one approach, automatically accounting for radiation dosing of the given patient 207 that results from imaging to determine at least one physical position of the given patient 207 can comprise, at least in part, using coarser calculation resolution when accounting for radiation dosing of the given patient that results from the aforementioned imaging than is used to determine radiation dosing of the given patient 207 that is attributable to therapeutic dosing. Such an approach can help accommodate daily patient set up variations by smoothing out the dose distribution attributable to imaging fields over the course of multiple treatments. In particular, a course dose calculation grid can simulate the effect of small daily set up variations. In addition, in many cases employing a same resolution standard as is used for standard treatment fields may result in an unrealistically sharp-based dose gradient that might cause unnecessary dose gradients in the treatment fields that might increase the possibility that the final delivered dose distribution will not match the planned dose distribution.

At optional block 105 this process 100 will accommodate using the resultant radiation-treatment plan that accommodates and accounts for image-based radiation dosing of the given patient 207 to conduct a radiation treatment session with that patient 207. These teachings will accommodate so employing the radiation-treatment plan by the same control circuit 201 that formed the radiation-treatment plan per the foregoing or a different control circuit of convenience.

At block 106 this process 100 will also optionally accommodate, during the administration of the radiation-treatment plan, detecting any alterations to the imaging plan for that radiation treatment session. Examples of alterations include, but are not limited to, adding at least one additional imaging episode for that radiation treatment session and/or skipping one or more scheduled or otherwise planned imaging episodes for that radiation treatment session. Adding an imaging episode can of course result in additional radiation exposure while skipping an imaging episode can result in a reduction in radiation exposure. At block 107 this process 100 will optionally provide for modifying the radiation-treatment plan, when conducting the radiation treatment session, to include an alteration to the radiation treatment session imaging plan by, for example, modifying planned therapeutic radiation doses for that radiation treatment session.

As noted, these teachings are highly flexible in practice and will accommodate, for example, such variations as tracking the actual location of imaging beams and using that information to estimate the imaging dose for each fraction (such as a daily set up fraction) separately. Those fraction-based imaging doses can then be considered in the dose accumulation to thereby account for their relative contribution of patient-experienced radiation.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

What is claimed is:

1. A method to facilitate using a radiation-treatment plan to treat a treatment target in a given patient that takes into account imaging-based dosing of the given patient, comprising:
    accessing information regarding radiation dosing to which the given patient was exposed from imaging to determine at least one physical position of the given patient;
    while optimizing the radiation-treatment plan for the given patient, automatically using the information regarding the radiation dosing by taking the radiation dosing into account as part of a base dose distribution for the given patient, wherein using the information regarding the radiation dosing by taking the radiation dosing into account comprises, at least in part, taking the radiation dosing into account by using courser calculation resolution for the radiation dosing that results from the imaging than is used to determine radiation dosing of the given patient that results from therapeutic dosing; and
    using the radiation-treatment plan with a therapeutic radiation beam source to conduct a radiation treatment session with the given patient.

2. The method of claim 1, wherein the imaging comprises obtaining images using megavoltage range radiation.

3. The method of claim 1, wherein using the information regarding the radiation dosing by taking the radiation dosing into account comprises, at least in part, automatically adjusting therapeutic dosing of the given patient as a function of the radiation dosing of the given patient that results from imaging.

4. The method of claim 1, wherein automatically using the information regarding the radiation dosing by taking the radiation dosing into account comprises, at least in part, using at least one imaging dose model to determine a radiation dose that is due to the imaging.

5. The method of claim 1, wherein automatically using the information regarding the radiation dosing by taking the radiation dosing into account comprises, at least in part, accounting for multiple instances of imaging that each has a corresponding radiation dosing of the given patient.

6. The method of claim 5, wherein accounting for multiple instances of imaging that each has a corresponding radiation dosing of the given patient includes accounting for both prospective and completed instances of the imaging.

7. The method of claim 1, wherein automatically using the information regarding the radiation dosing by taking the radiation dosing into account comprises, at least in part, using information regarding actual imaging-beam locations.

8. The method of claim 7, wherein using information regarding actual imaging-beam locations comprises, at least in part, using information regarding actual imaging-beam locations on a patient setup-by-setup basis.

9. The method of claim 7, wherein using information regarding actual imaging-beam locations comprises, at least in part, using the actual imaging-beam locations to estimate corresponding radiation dosages.

10. The method of claim 7, wherein using information regarding actual imaging-beam locations comprises, at least in part, using at least one radiobiological model to estimate accumulative effective radiation doses.

11. The method of claim 10 wherein using at least one radiobiological model to estimate accumulative effective radiation doses comprises, at least in part, using at least one radiobiological model to estimate accumulative effective radiation doses based upon a plurality of imaging episodes that use at least partially-different actual imaging-beam locations.

12. The method of claim 1, further comprising:
    modifying the radiation-treatment plan when conducting the radiation treatment session includes an alteration to an imaging plan for that radiation treatment session.

13. The method of claim 12, wherein the alteration to the imaging plan comprises at least one of:
    at least one additional imaging episode for that radiation treatment session;
    at least one skipped imaging episode for that radiation treatment session.

14. The method of claim 1, wherein using the information regarding the radiation dosing by taking the radiation dosing into account comprises accounting for the radiation dosing of the given patient that results from imaging in monitor units (MU's).

* * * * *